(12) United States Patent
Levine et al.

(10) Patent No.: US 7,521,403 B2
(45) Date of Patent: Apr. 21, 2009

(54) ALKYLAMINOACETAMIDE LUBRICANT ADDITIVES

(75) Inventors: Jeffrey A. Levine, White Plains, NY (US); Si Wu, White Plains, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 580 days.

(21) Appl. No.: 11/222,198

(22) Filed: Sep. 8, 2005

(65) Prior Publication Data

US 2006/0058202 A1 Mar. 16, 2006

Related U.S. Application Data

(60) Provisional application No. 60/609,426, filed on Sep. 13, 2004.

(51) Int. Cl.
*C10M 173/02* (2006.01)
(52) U.S. Cl. ...................................... 508/554; 508/551
(58) Field of Classification Search ................. 508/551, 508/554; 564/153, 160, 193, 197
See application file for complete search history.

(56) References Cited

U.S. PATENT DOCUMENTS

| | | | | |
|---|---|---|---|---|
| 2,191,978 A | 2/1940 | Balle et al. | ................... | 260/482 |
| 2,256,186 A | 9/1941 | Balle et al. | ................... | 260/561 |
| 2,411,662 A | 11/1946 | Martin et al. | ................ | 260/561 |
| 2,516,674 A | 7/1950 | Bruce et al. | ................. | 260/561 |
| 2,548,863 A | 4/1951 | Bruce et al. | ................. | 260/561 |
| 2,746,901 A | 5/1956 | Bruce et al. | .................... | 167/65 |
| 2,830,019 A | 4/1958 | Fields et al. | ............... | 252/33.6 |
| 2,954,342 A | 9/1960 | Hotten | ......................... | 252/32 |
| 3,024,277 A | 3/1962 | Hotten | ......................... | 260/534 |
| 3,173,770 A | 3/1965 | Thompson et al. | ............. | 44/63 |
| 3,202,491 A | 8/1965 | Maxwell et al. | ................ | 44/63 |
| 3,214,377 A | 10/1965 | Hotten | ....................... | 252/33.6 |
| 3,407,051 A | 10/1968 | Thompson et al. | ............. | 44/63 |
| 3,449,097 A | 6/1969 | Andress, Jr. | .................... | 44/71 |
| 4,242,101 A | 12/1980 | Vogel et al. | ..................... | 44/58 |
| 4,249,912 A | 2/1981 | Holtz et al. | ..................... | 44/71 |
| 4,358,387 A | 11/1982 | Zoleski et al. | ............. | 252/33.4 |
| 4,639,468 A * | 1/1987 | Roncucci et al. | ............ | 514/620 |
| 4,801,618 A | 1/1989 | White | ........................ | 514/616 |
| 5,071,445 A | 12/1991 | Oppenlaender et al. | ....... | 44/408 |
| 5,282,872 A | 2/1994 | Oppenlaender et al. | ....... | 44/403 |
| 5,376,155 A | 12/1994 | Dralle-Voss et al. | .......... | 44/408 |

FOREIGN PATENT DOCUMENTS

EP 0835924 4/1998

OTHER PUBLICATIONS

D. Erne et al., Helvetica Chimica Acta, vol. 63, Fasc. 8, (1980), No. 237, pp. 2264-2270.

Chem. Abstract 1972:541311 for JP 47004941, Feb. 1972.
Chem. Abstract 1971:65418 for JP 45037547, Nov. 1970.

* cited by examiner

*Primary Examiner*—Glenn A Caldarola
*Assistant Examiner*—Taiwo Oladapo
(74) *Attorney, Agent, or Firm*—Tyler A. Stevenson

(57) ABSTRACT

Alkylamine, alkylenedi-, alkylenetri- or alkylenetetra-amine derivatives of N-alkyl-halo-acetamides, are useful as ashless, phosphorus-free and sulfur-free antiwear and friction modifying additives for lubricating oils. The additives are of the formula (I), (II) or (III)

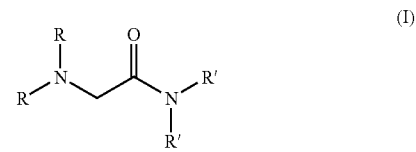

(I)

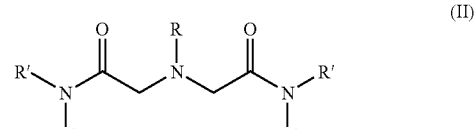

(II)

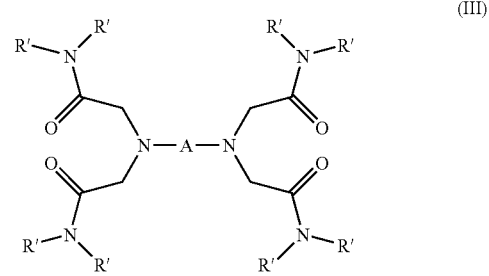

(III)

where A is alkylene of from 2 to 6 carbon atoms or is a group

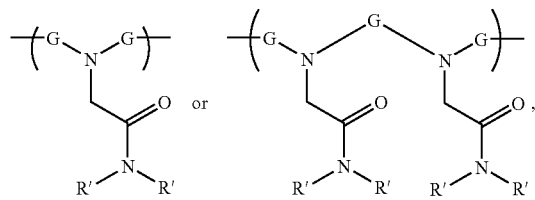

G, each independently, is alkylene of 2 to 6 carbon atoms, R, each independently, is alkyl or alkenyl of 1 to 8 carbon atoms and R', each independently, is hydrogen or alkyl or alkenyl or 1 to 24 carbon atoms, where if an amide nitrogen is monosubstituted by alkyl or alkenyl, said alkyl or alkenyl is from 8 to 24 carbon atoms, where if an amide nitrogen is disubstituted by alkyl or alkenyl, the total carbon atoms of said alkyls or alkenyls combined are from 8 to 18 carbon atoms, and where each amide nitrogen is either mono- or disubstituted by alkyl or alkenyl.

14 Claims, No Drawings

ALKYLAMINOACETAMIDE LUBRICANT ADDITIVES

This application claims benefit under 35 USC 119(e) of U.S. provisional app. No. 60/609,426, filed Sep. 13, 2004.

The present invention is aimed at the use of alkylaminoacetamides, that is alkylamine, alkylenedi-, alkylenetri- or alkylenetetra-amine derivatives of N-alkyl-halo-acetamides, as ashless, phosphorus-free and sulfur-free antiwear and friction modifying additives for lubricating oils.

BACKGROUND

*Helv. Chim. Acta* 1980, 63(8), 2264-2270 teaches electrically neutral lipophilic di-, tri- and tetra-amides containing tertiary amine nitrogen atoms as ligands in polymeric membranes.

U.S. Pat. No. 2,746,901 relates to salts of alpha-di-alkylamino-N,N-di-alkyl acetamides for treating dysmenorrhea.

U.S. Pat. No. 2,256,186 teaches quaternary nitrogen compounds prepared by causing a halogencarboxylic acid amide to act upon a disubstituted aminoacylamide obtainable by reaction of halogenacylamides with secondary amines. The use of the quaternary compounds are as softeners for textiles and as agents for the improvement of the fastness qualities of substantive dyeings.

JP47004941 teaches ethylenediamine tetra(N,N-dialkylacetamide) compounds as heat stabilizers for acrylic fibers. Alkyl is ethyl or butyl.

JP45037547 teaches ethylenediamine tetra(N,N-dialkylacetamide) compounds as additives in acrylic fibers. Alkyl is $C_1$-$C_4$.

U.S. Pat. No. 4,801,618 discloses ethylenediamine tetra(N, N-dialkylacetamide) compounds for improving feed utilization and lactation in ruminant animals. Alkyl is straight or branched chain of one to six carbon atoms.

U.S. Pat. No. 3,214,377 discloses phenylamides of organoamine polyacetic acids as antioxidants for lubricating oils. The preferred antioxidant is ethylenediamine tetra(N-benzylacetamide).

EP835924 relates to the use of carboxylic acids, metal salts of carboxylic acids, amine salts of carboxylic acids and carboxylic acid amides as lubricating oil additives.

U.S. Pat. Nos. 2,830,019 and 3,449,097 disclose hydrocarbon oil compositions containing an additive which is the salt of an amine and an amino-carboxylic acid.

U.S. Pat. No. 4,249,912 teaches aminoamide detergent additives for fuels.

U.S. Pat. No. 2,954,342 teaches certain amides of ethylenediaminetetraacetic acid as antioxidants for lubricating oils.

U.S. Pat. No. 3,173,770 relates to certain amides of ethylenediaminetetraacetic acid as metal deactivators for fuels.

U.S. Pat. Nos. 3,202,491 and 3,407,051 relate to fuel oils that contain imide-amide reaction products of ethylenediaminetetraacetic acid and primary amines.

U.S. Pat. No. 3,024,277 as well teaches certain amides of ethylenediaminetetraacetic acid as antioxidants for lubricants.

U.S. Pat. No. 4,242,101 discloses the use of imides or amide-imides which are the reaction products of nitrilotriacetic acid or of ethylenediaminetetraacetic acid with amines in fuels for gasoline engines.

U.S. Pat. Nos. 5,282,872 and 5,071,445 disclose amide, amide/ammonium salt or ammonium salt compounds of an aminoalkylene polycarboxylic acid and a secondary fatty amine as additives in fuels.

U.S. Pat. No. 5,376,155 teaches the reaction products of aminoalkylenecarboxylic acids with primary or secondary amines as paraffin dispersants in mineral oils.

It has now been found that certain N-alkylaminoacetamide or alkylenedi-, alkylenetri- or alkylenetetra-amine acetamide compounds are excellent antiwear and friction modifying additives for lubricating oils.

SUMMARY OF THE INVENTION

Disclosed is a composition comprising
a lubricant and
an effective antiwear or friction modifying amount of one or more additive compounds selected from the group consisting of
N-alkylaminoacetamide compounds of formula (I) or (II) and
alkylenedi-, alkylenetri- or alkylenetetra-amine acetamide compounds of formula (III)

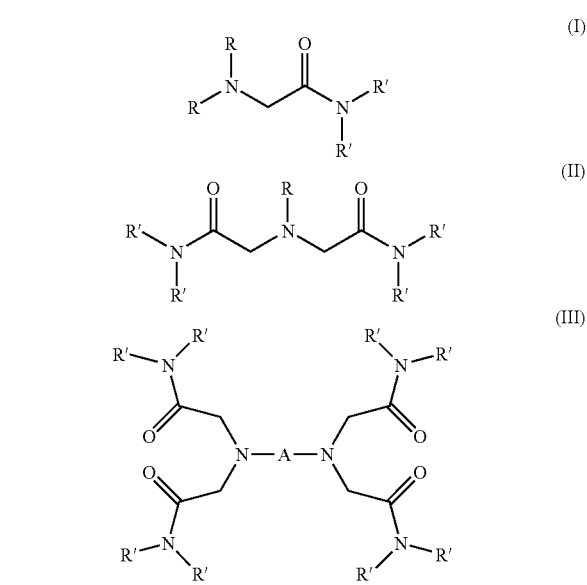

where
A is alkylene of from 2 to 6 carbon atoms or is a group

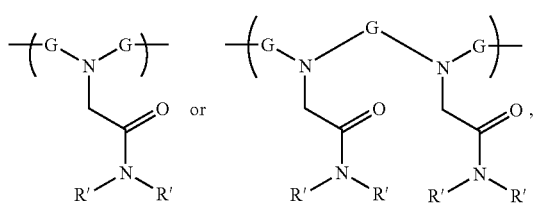

G, each independently, is alkylene of 2 to 6 carbon atoms,
R, each independently, is alkyl or alkenyl of 1 to 8 carbon atoms and
R', each independently, is hydrogen or alkyl or alkenyl or 1 to 24 carbon atoms, where if an amide nitrogen is monosubstituted by alkyl or alkenyl, said alkyl or alkenyl is from 8 to 24 carbon atoms, where if an amide nitrogen is disubstituted by alkyl or alkenyl, the total carbon atoms of said alkyls or alkenyls combined are from 8 to 18 carbon atoms, and where each amide nitrogen is either mono- or disubstituted by alkyl or alkenyl and
where the compounds of formula (I), (II) or (III) are present from about 0.15% to about 10% by weight, based on the weight of the lubricant.

For example, if an amide nitrogen is disubstituted by alkyl or alkenyl, the total carbon atoms of said alkyls or alkenyls combined are from 14 to 18 carbon atoms.

Many of the N-alkylaminoacetamide or alkylenedi-, tri- or tetra-amine acetamide compounds are new.

Therefore further disclosed are alkylaminoacetamide compounds of the formula (I)

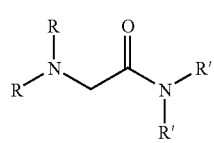
(I)

where

R, each independently, is alkyl or alkenyl of 5 to 8 carbon atoms and

R', each independently, is hydrogen or alkyl or alkenyl of 1 to 24 carbon atoms, where if the amide nitrogen is monosubstituted by alkyl or alkenyl, said alkyl or alkenyl is from 8 to 24 carbon atoms, where if an amide nitrogen is disubstituted by alkyl or alkenyl, the total carbon atoms of said alkyls or alkenyls combined are from 14 to 18 carbon atoms, and where the amide nitrogen is either mono- or disubstituted by alkyl or alkenyl.

Also disclosed are N-alkylaminoacetamide compounds of formula (II)

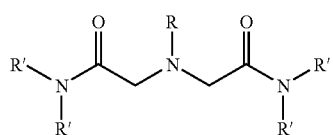
(II)

where

R is alkyl or alkenyl of 1 to 8 carbon atoms and

R', each independently, is hydrogen, alkyl or alkenyl or 1 to 24 carbon atoms, where if an amide nitrogen is monosubstituted by alkyl or alkenyl, said alkyl or alkenyl is from 8 to 24 carbon atoms, where if an amide nitrogen is disubstituted by alkyl or alkenyl, the total carbon atoms of said alkyls or alkenyls combined are from 8 to 18 carbon atoms, and where each amide nitrogen is either mono- or disubstituted by alkyl or alkenyl.

Also disclosed are alkylenedi-, alkylenetri- or alkylenetetra-amine acetamide compounds of the formula (III)

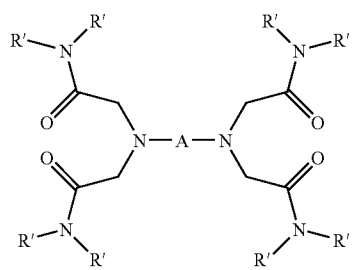
(III)

where

A is as previously described,

R', each independently, is alkyl or alkenyl of 1 to 24 carbon atoms, where for each amide group, the total carbon atoms of said alkyls or alkenyls combined are from 14 to 18 carbon atoms.

DETAILED DISCLOSURE

The present N-alkylaminoacetamide compounds and alkylenedi-, alkylenetri- or alkylenetetra-amine acetamide compounds are prepared for example by alkylation of primary or secondary amines with mono- or di-alkyl substituted haloacetamides according to the following sheme:

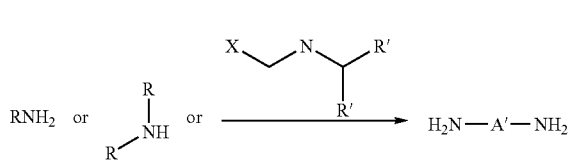

where

A' is alkylene of from 2 to 6 carbon atoms or is a group

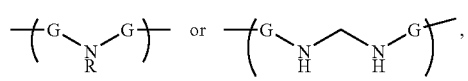

X is Cl, Br or I and

R and R' and G are as previously defined.

Several chloroacetamides are described in for example U.S. Pat. Nos. 2,746,901 and 4,801,618, the disclosures of which are hereby incorporated by reference. The present compounds of formulae (I) and (II) may be prepared according to methods disclosed in these references. Haloacetamides are also described by van Esch, et al., *J. Org. Chem.* 1995, 60, 1599-1610, and by Weaver, et al., *J. Am. Chem. Soc.* 1947, 69, 515-516.

The present compounds of formulae (I), (II) and (III) are prepared by reacting a haloacetamide with an appropriate amine or di-, tri- or tetra-amine in the ratio of about 1 molar equivalent of haloacetamide per reactive aminic hydrogen. For example butylamine has two reactive aminic hydrogens, dibutylamine has one reactive aminic hydrogen, and ethylenediamine has four reactive aminic hydrogens. The reagents are mixed neat or in a suitable solvent, at a suitable temperature and for a suitable time to complete the reaction. The reagents are mixed in the presence of an inorganic base, for example sodium carbonate.

The present compounds prepared in this way are not salts. They do not contain any ammonium salts. They do not contain any ammonium carboxylate salts which would exist if prepared for example from reaction of an alkylamine and an aminoalkylcarboxylic acid.

In the present additives of formulae (I)-(III), R is for example alkyl or alkenyl of 5 to 8 carbon atoms. A and G are for example ethylene, propylene, hexamethylene or 2-methylpentylene. For example, each amide is disubstituted by alkyl or alkenyl. For example, each R' is the same. For example, each R' is straight or branched chain alkyl or alkenyl of 7 to 9 carbon atoms. For example, one R' of each amide is hydrogen and the other is straight or branched chain alkyl or alkenyl of 14 to 18 carbon atoms.

For example, in the present additives, each of the amide nitrogens are disubstituted by alkyl or alkenyl and the total carbon atoms of said alkyls or alkenyls for each amide combined are from 14 to 18 carbon atoms, that is to say, each R' is straight or branched chain alkyl or alkenyl of 7 to 9 carbon atoms.

For instance, in the present additives, R is n-octyl and each R' is 2-ethylhexyl or n-octyl or one R' of each amide is hydrogen and the other is oleyl, n-octyl, t-octyl or dodecyl.

Alkyl is straight or branched chain and is for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

Alkenyl is also straight or branched and is an ethylenically unsaturated version of alkyl, for example allyl, oleyl, docosenyl, and the like.

Alkylene is straight or branched and is for example ethylene, propylene, methylethylene, tetramethylene, pentamethylene or hexamethylene.

Suitable amines are for example octylamine, dioctylamine, butylamine, dibutylamine, ethylenediamine, diethylenetriamine, dipropylenetriamine, $H_2N-(CH_2)_3NH(CH_2)_2NH(CH_2)_3NH_2$, and the like.

The present additive compounds of formulae (I)-(III), that is the present additives, are highly soluble in the lubricant, for example are soluble at 1%, 2% or for example at 5% on a weight/weight basis at room temperature.

The present additives, when employed in lubricants (lubricating oils) for internal combustion engines, serve both to reduce wear of the engine's moving parts and to reduce friction. The additives provide an economic method to accomplish desired antiwear and reduced friction properties without the use of a metal such as Zn, or the elements S or P, enabling a significant reduction or the elimination of P, S, and Zn containing additives.

The present lubricants are for example those employed in internal combustion engines. The present lubricants have necessary lubricating viscosity and are for example mineral oils or are synthetic and mixtures thereof.

Greases or other solid lubricants are also lubricating oils according to this invention.

Synthetic hydrocarbon oils include long chain alkanes such as cetanes and olefin polymers such as trimer and tetramers of octane and decene. These synthetic oils can be mixed with 1) ester oils such as pentaerythritol esters of monocarboxylic acids having about 2 to 20 carbon atoms, 2) polyglycol ethers, 3) polyacetals and 4) siloxane fluids. Useful among the synthetic esters are those made from polycarboxylic acids and monohydric alcohols. For example, ester fluids made from pentaerythritol or mixtures thereof with di- and tripentaerythritol, and an aliphatic monocarboxylic acid containing from 1 to 20 carbon atoms, or mixtures of such acids. Other examples are ester fluids made from trimethylolpropane and an aliphatic monocarboxylic acid containing from 1 to 20 carbon atoms, or mixtures of such acids.

The present lubricating oils are also for example crude oil, industrial lubrication oils, cutting oil, metal working fluids and greases.

The additives of this invention are advantageously present in the lubricant at a level of for example from about 0.15% to about 10% by weight of lubricant. For example, the additives are present from about 0.15% to about 7%, from about 0.25% to about 5%, from about 0.5% to about 3%, or from about 0.75% to about 2% by weight of the lubricant. For example, the present additives are present from about 0.5% to about 5%, from about 0.5% to about 7%, or from about 0.5% to about 10% by weight, based on the weight of the lubricant.

It is contemplated that in lubricating compositions operated under extremely adverse conditions, such as lubricating compositions for marine diesel engines, that the additives of this invention may be present in amounts of up to about 30% by weight, or more, of the total weight of the lubricating composition.

The lubiricating oils in accordance with the invention may additionally include other additives, which are added in order to improve still further the basic properties of these formulations; such additives include antioxidants, metal passivators, rust inhibitors, corrosion inhibitors, viscosity index improvers, extreme pressure agents, pour point depressants, solid lubricants, dispersants, detergents, antifoams, color stabilizers, further high-pressure additives, demulsifiers, antiwear additives and additives which reduce the coefficient of friction. Such additives are added in the customary amounts in each case in the range from in each case about 0.01% to 10.0% by weight, based on the lubricating oil.

The text below gives examples of such additional additives:

Examples of antioxidants:

1) alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methylphenol, 2-(a-methyl-cyclohexyl)-4,6-dimethylphenol, 2,6-di-octadecyl-4-methylphenol, 2,4,6-tricyclo-hexylphenol, 2,6-di-tert-butyl-4-methoxymethylphenol, linear or sidechain-branched nonylphenols, for example 2,6-di-nonyl-4-methylphenol, 2,4-dimethyl-6-(1'-methyl-undec-1'-yl)phenol, 2,4-dimethyl-6-(1'-methylheptadec-1'-yl)phenol, 2,4-dimethyl-6-(1'-methyltridec-1'-yl)phenol or mixtures thereof;

2) alkylthiomethylphenols, for example 2,4-di-octylthiomethyl-6-tert-butylphenol, 2,4-di-octylthiomethyl-6-methylphenol, 2,4-di-octylthiomethyl-6-ethylphenol or 2,6-di-dodecylthiomethyl-4-nonylphenol;

3) hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl stearate or bis(3,5-di-tert-butyl-4-hydroxyphenyl) adipate;

4) tocopherols, for example α-, β-, γ- or δ-tocopherol or mixtures thereof (vitamin E);

5) hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis-(6-tert-butyl-2-methylphenol), 4,4'-thiobis(3,6-di-sec-amylphenol) or 4,4'-bis(2,6-dimethyl-4-hydroxyphenyl) disulfide;

6) alkylidenebisphenols, for example 2,2'-methylenebis(6-tert-butyl-4-methylphenol), 2,2'-methylenebis(6-tert-butyl-4-ethylphenol), 2,2'-methylenebis(4-methyl-6-(alpha-methylcyclohexyl)-phenol), 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis(6-(alpha-methylbenzyl)-4-nonylphenol), 2,2'-methylenebis(6-(alpha,alpha-dimethylbenzyl)-4-nonylphenol), 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4- hydroxy-2-methylphenyl)butane, 1,1-bis(5-tert-butyl-4-hydroxy-2-methylphenyl)-3-n-dodecylmercaptobutane, ethylene glycol bis(3,3-bis(3'-tert-butyl-4'-hydroxyphenyl)butyrate), bis(3-tert-butyl-4-hydroxy-5-methylphenyl)dicyclopentadiene, bis(2-(3'-tert-butyl-2'-hydroxy-5'-methylbenzyl)-6-tert-butyl-4-methylphenyl)terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane or 1,1,5,5-tetra(5-tert-butyl-4-hydroxy-2-methylphenyl)-pentane;

7) O- N- and S-benzyl compounds, for example 3,5,3',5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl)amine, bis(4-tert-butyl-3-hydroxy-2,6-dimethylbenzyl)dithioterephthalate, bis(3,5-di-tert-butyl-4-hydroxybenzyl) sulfide or isooctyl 3,5-di-tert-butyl-4-hydroxybenzylmercaptoacetate;

8) hydroxybenzylated malonates, for example—dioctadecyl 2,2-bis(3,5-di-tert-butyl-2-hydroxybenzyl)malonate, dioctadecyl 2-(3-tert-butyl-4-hydroxy-5-methylbenzyl)-malonate, di-dodecyl mercaptoethyl-2,2-bis(3,5-di-tert-butyl-4-hydroxybenzyl)-malonate or di(4-(1,1,3,3-tetramethylbutyl) phenyl)2,2-bis(3,5-di-tert-butyl-4-hydroxybenzyl)malonate;

9) aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene or 2,4,6-tris(3,5-di-tert-butyl-4-hydroxybenzyl)phenol;

10) triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)-isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine or 1,3,5-tris(3,5-dicyclohexyl-4-hydroxybenzyl)-isocyanurate;

11) benzylphosphonates, for example dimethyl 2,5-di-tert-butyl-4-hydroxybenzyl-phosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate or the calcium salt of the monoethyl ester of 3,5-di-tert-butyl-4-hydroxybenzylphosphonic acid;

12) acylaminophenols, for example 4-hydroxylauranilide, 4-hydroxystearanilide or octyl N-(3,5-di-tert-butyl-4-hydroxyphenyl)carbamate;

13) esters of β-(3,5-di-tert-butyl-4-hydroxyphenyl)propionic acid, β-(5-tert-butyl-4-hydroxy-3-methylphenyl)propionic acid, β-(3,5-dicyclohexyl-4-hydroxyphenyl)-propionic acid, 3,5-di-tert-butyl-4-hydroxyphenylacetic acid or β-(5-tert-butyl-4-hydroxyphenyl)-3-thiabutyric acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethyl-hexanediol, trimethylolpropane, 4-hydroxymethyl-1-phospha-2,6,7-trioxabicyclo(2.2.2)octane, glycerol or transesterification products based on natural triglycerides of, for example, coconut oil, rape seed oil, sunflower oil or colza oil;

14) amides of β-(3,5-di-tert-butyl-4-hydroxyphenyl)propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine or N,N'-bis(3,5-di-tert-butyl-4-hydroxyphenylpropionyl)hydrazine;

15) ascorbic acid (vitamin C);

16) amine-type antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylendiamine, N,N'-dicyclohexyl-p-phenylenediamine, N,N'-diphenyl-p-phenylenediamine, N,N'-di-(naphth-2-yl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, e.g. p,p'-di-tert-octyidiphenyl-amine, 4-n-butylaminophenol, 4-butyrylamino-phenol, 4-nonanoylamino-phenol, 4-dodecanoylaminophenol, 4-octadecanoylamino-phenol, di-(4-methoxyphenyl)-amine, 2,6-di-tert-butyl-4-dimethylaminomethyl-phenol, 2,4'-diamino-diphenylmethane, 4,4'-diamino-diphenylmethane, N,N,N',N'-tetramethyl-4,4'-diamino-diphenylmethane, 1,2-di-((2-methyl-phenyl)-amino)-ethane, 1,2-di-(phenylamino)propane, (o-tolyl) biguanide, di(4-(1',3'-dimethyl-butyl)-phenyl)amine, tert-octylated N-phenyl-1-naphthylamine, a mixture of mono- and dialkylated tert-butyl/tert-octyidiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, mixtures of mono- and dialkylated tert-butyidiphenylamines, 2,3-dihydro-3,3-dimethyl-4H-1,4-benzothiazine, phenothiazine, a mixture of mono- and dialkylated tert-butyl/tert-octyl-phenothiazines, a mixture of mono- and dialkylated tert-octyl-phenothiazines, N-allylphenothiazine, N,N,N',N'-tetraphenyl-1,4-diaminobut-2-ene, N,N-bis-(2,2,6,6-tetramethylpiperidin-4-yl)hexamethylenediamine, bis-(2,2,6,6-tetramethylpiperidin-4-yl) sebacate, 2,2,6,6-tetramethylpiperidin-4-one or 2,2,6,6-tetramethylpiperidin-4-ol; and 17) aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,1-trithiatridecane or 2,2,15,15-tetramethyl-5,12-dihydroxy-3,7,10,14-tetrathiahexadecane.

Examples of metal passivators, for example for copper, are:

1) benzotriazoles and their derivatives, for example 4- or 5-alkylbenzotriazoles (e.g. tolutriazole) and derivatives thereof, 4,5,6,7-tetrahydrobenzotriazole, 5,5'-methylenebisbenzotriazole; Mannich bases of benzotriazole or tolutriazole, such as 1-(di(2-ethylhexyl)aminomethyl)tolutriazole and 1-(di(2-ethylhexyl)aminomethyl)-benzotriazole; alkoxyalkylbenzotriazoles, such as 1-(nonyloxymethyl)-benzotriazole, 1-(1-butoxyethyl)-benzotriazole and 1-(1-cyclohexyloxybutyl)-tolutriazole;

2) 1,2,4-triazoles and derivatives thereof, for example 3-alkyl(or aryl)-1,2,4-triazoles, Mannich bases of 1,2,4-triazoles such as 1-(di(2-ethylhexyl)aminomethyl)-1,2,4-triazole; alkoxyalkyl-1,2,4-triazoles such as 1-(1-butoxyethyl)-1,2,4-triazole; acylated 3-amino-1,2,4-triazoles;

3) imidazole derivatives, for example 4,4'-methylenebis(2-undecyl-5-methyl-imidazole), bis((N-methyl)imidazol-2-yl) carbinol octyl ether;

4) sulfur-containing heterocyclic compounds, for example 2-mercaptobenzothiazole, 2,5-dimercapto-1,3,4-thiadiazole, 2,5-dimercaptobenzothiadiazole and derivatives thereof; 3,5-bis(di(2-ethylhexyl)aminomethyl)-1,3,4-thiadiazolin-2-one; and 5) amino compounds, for example salicylidenepropylenediamine, salicylaminoguanidine and salts thereof.

Examples of rust inhibitors are:
1) organic acids, their esters, metal salts, amine salts and anhydrides, for example alkyl- and alkenylsuccinic acids and the partial esters thereof with alcohols, diols or hydroxycarboxylic acids, partial amides of alkyl- and alkenylsuccinic acids, 4-nonylphenoxyacetic acid, alkoxy- and alkoxyethoxycarboxylic acids, such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(2-carboxyethyl)-1-dodecyl-3-methylglycerine and its salts, especially sodium and triethanolamine salts;

2) nitrogen-containing compounds, for example:
  i) primary, secondary or tertiary aliphatic or cycloaliphatic amines and amine salts of organic and inorganic acids, for example oil-soluble alkylammonium carboxylates, and also 1-(N,N-bis(2-hydroxyethyl)amino-3-(4-nonylphenoxy)propan-2-ol;
  ii) heterocyclic compounds, for example: substituted imidazolines and oxazolines, 2-heptadecenyl-1-(2-hydroxyethyl)-imidazoline;

3) phosphorus-containing compounds, for example Amine salts of phosphoric acid partial esters or phosphonic acid partial esters, zinc dialkyldithiophosphates;

4) sulfur-containing compounds, for example: barium dinonylnaphthalene-sulfonates, calcium petroleumsulfonates, alkylthio-substituted aliphatic carboxylic acids, esters of aliphatic 2-sulfocarboxylic acids and salts thereof; and 5) glycerine derivatives, for example: glycerine monooleate, 1-(alkylphenoxy)-3-(2-hydroxyethyl)glycerines, 1-(alkylphenoxy)-3-(2,3-dihydroxypropyl)glycerines, 2-carboxyalkyl-1,3-dialkylglycerines.

Examples of viscosity index improvers are:
polyacrylates, polymethacrylates, vinylpyrrolidone/methacrylate copolymers, polyvinylpyrrolidones, polybutenes, olefin copolymers, styrene/acrylate copolymers, polyethers.

Examples of pour point depressants are:
polymethacrylate, alkylated naphthalene derivatives.

Examples of dispersants/surfactants are:
polybutenylsuccinamides or -imides, polybutenylphosphonic acid derivatives, and basic magnesium, calcium and barium sulfonates, phenolates and salicylates.

Examples of antifoams are: silicone oils and polymethocrylen.

The demulsifiers are for example selected from:
polyetherpolyols and dinonylnaphthalenesulfonates.

The friction modifiers are for example selected from:
fatty acids and their derivatives (i.e. natural esters of fatty acids such as glycerol monooleate), amides, imides and amines (i.e. oleylamine), sulfur containing organomolybdenum dithiocarbamates, sulfur-phosphorus containing organomolybdenum dithiophosphates, sulfur-nitrogen containing organomolybdenum compounds based on dispersants, molybdenum carboxylate salts, molybdenum-amine complexes, molybdenum amine/alcohol/amid complexes and molybdenum cluster compounds, Teflon™ and molybdenum disulfide.

Examples of additional antiwear additives are:
sulfur- and/or phosphorus- and/or halogen-containing compounds, such as sulfurized olefins and vegetable oils, zinc dialkyldithiophosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, di-(2-ethylhexyl)-aminomethyltolyltriazole, derivatives of 2,5-dimercapto-1,3,4-thiadiazole, ethyl(bisisopropyloxyphosphinothioyl)thiopropionate, triphenyl thiophosphate (triphenyl phosphorothioate), tris(alkylphenyl) phosphorothioates and mixtures thereof (for example tris(isononylphenyl) phosphorothioate), diphenylmononoylphenyl phosphorothioate, isobutylphenyl diphenyl phosphorothioate, the dodecylamine salt of 3-hydroxy-1,3-thiaphosphetan 3-oxide, trithiophosphoric acid 5,5,5-trisisooctyl 2-acetate, derivatives of 2-mercaptobenzothiazole, such as 1-N,N-bis(2-ethylhexyl)aminomethyl-2-mercapto-1H-1,3-benzothiazole, and ethoxycarbonyl 5-octyldithiocarbamate;

dihydrocarbyl dithiophosphate metal salts where the metal is aluminum, lead, tin manganese, cobalt, nickel, zinc or copper, but most often zinc. The zinc salt (zinc dialkyl dithiophosphate) is represented as

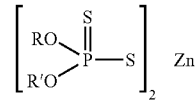

where R and R' are independently $C_1$-$C_{20}$ alkyl, $C_3$-$C_{20}$ alkenyl, $C_5$-$C_{12}$ cycloalkyl, $C_7$-$C_{13}$ aralkyl or $C_6$-$C_{10}$ aryl, for example R and R' are independently $C_1$-$C_{12}$ alkyl;

antiwear additives as described in U.S. Pat. Nos. 4,584,021; 5,798,321; 5,750,478; 5,801,130; 4,191,666; 4,720,288; 4,025,288; 4,025,583 and WO 095/20592, which U.S. patents are incorporated herein by reference; amines for example polyalkylene amines such as ethylene diamine, diethylene triamine, triethylene tetraamine, tetraethylene pentamine, pentaethylene hexamine, nonaethylene decamine and aryl amines as described in U.S. Pat. No. 4,267,063, herein incorporated by reference; salts of amine phosphates comprising specialty amines and mixed mono- and di-acid phosphates; the mono- and di-acid phosphate amines have the structural formulae:

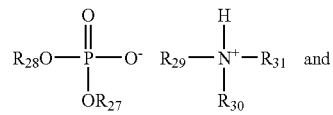

-continued

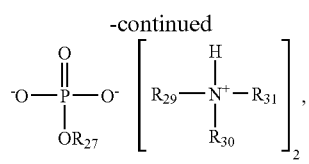

wherein $R_{27}$ is hydrogen, $C_1$-$C_{25}$ linear or branched chain alkyl which is unsubstituted or substituted by one or more $C_1$-$C_6$ alkoxy groups, a saturated acyclic or alicyclic group, or aryl;

$R_{28}$ is $C_1$-$C_{25}$ linear or branched chain alkyl which is unsubstituted or substituted by one or more $C_1$-$C_6$ alkoxy groups, a saturated acyclic or alicyclic group, or aryl;

$R_{29}$ is hydrogen, $C_1$-$C_{25}$ linear or branched chain alkyl, a saturated or unsaturated acyclic or alicyclic group, or aryl; and are hydrogen or $C_1$-$C_{12}$ linear or branched chain alkyl; and $R_{30}$ and $R_{31}$ are, each independently of the other, $C_1$-$C_{25}$ linear or branched chain alkyl, a saturated or unsaturated acyclic or alicyclic group, or aryl. Preferably, $R_{27}$ and $R_{28}$ are linear or branched $C_1$-$C_{12}$ alkyl; and $R_{29}$, $R_{30}$ and $R_{31}$ are linear or branched $C_1$-$C_{18}$ alkyl;

a mixture of amine phosphates, CAS# 80939-62-4 has been found to be very useful, particularly by enhancing the wear performance of the base oil such that it meets stringent military performance specifications;

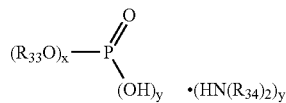

wherein $R_{33}$ is n-hexyl, $R_{34}$ is $C_{11}$-$C_{14}$ branched alkyl, and when x=1 then y=2; when x=2 then y=1;

other conventional antiwear additives are compounds of the formula

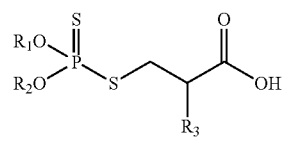

in which $R_1$ and $R_2$ independently of one another are $C_3$-$C_{18}$ alkyl, $C_5$-$C_{12}$ cycloalkyl, $C_5$-$C_6$ cycloalkylmethyl, $C_9$-$C_{10}$ bicycloalkylmethyl, $C_9$-$C_{10}$ tricycloalkylmethyl, phenyl or $C_7$-$C_{24}$ alkylphenyl or together are $(CH_3)_2C(CH_2)_2$, $R_3$ is hydrogen or methyl.

The present additives of formulae (I)-(III) can be introduced into the lubricating oil in manners known per se. The compounds are readily soluble in oils. They may be added directly to the lubricating oil or they can be diluted with a substantially inert, normally liquid organic diluent such as naphtha, benzene, toluene, xylene or a normally liquid oil to form an additive concentrate or masterbatch. These concentrates generally contain from about 10% to about 90% by weight additive and may contain one or more other additional additives. The present additives may be introduced as part of an additive package.

The present invention is further illustrated by the following Examples. Unless otherwise indicated, parts and percentages are by weight.

EXAMPLE 1

Ethylenediamine tetra-N-n-octylacetamide

To a stirred mixture of 2.80 g of ethylenediamine, 20.06 g of sodium carbonate, and 100 mg of potassium iodide in 100 mL of acetonitrile is added a solution of 38.35 g of 2-chloro-N-n-octylacetamide. After being stirred at ambient temperature for 18 hours, the mixture is heated at reflux for 5 days. After cooling, the mixture is partitioned between 400 mL of dichloromethane and 250 mL of water. The aqueous phase is further extracted with 200 mL of dichloromethane, and the combined organic extract is washed with water (200 mL), then brine (200 mL), dried over anhydrous sodium sulfate, and the solvent removed in vacuo. The resulting residue is recrystallized from ethyl acetate to give the product as a pale yellow fibrous wax.

EXAMPLE 2

Ethylenediamine tetra-N,N-di-n-octylacetamide

A mixture of 78.7 g of 2-chloro-N,N-dioctylacetamide, 3.7 g of ethylenediamine and 26.2 g of sodium carbonate in 300 mL of N,N-dimethylacetamide is heated at 90° C. for 3 hours, then heated at 120° C. for another 16 hours. The mixture is cooled, washed with water, extracted with hexane and dried over sodium sulfate. The hexanes are removed in vacuo to give 74.9 g of product as a viscous yellow liquid.

One-Pot Procedure:

To a rapidly stirred mixture of di-n-octylamine (25.03 g), xylenes (25 mL), $Na_2CO_3$ (12.5 g) and water (125 mL) is added chloroacetyl chloride (12.4 g) dropwise over 20 min. Intermittent cooling is applied to maintain temperature between 20-25° C. After completion of addition, the mixture is stirred for 30 min. The phases are allowed to separate and the lower aqueous phase removed. N,N-Dimethylacetamide (25 mL), ethylenediamine (1.55 g), and $Na_2CO_3$ (12.5 g) are added and the mixture heated with stirring to 120° C. The reaction is heated for 18 hrs, allowed to cool, then mixed with water (125 mL) to dissolve salts and DMAc, and the aqueous phase is removed. The solvents are removed in vacuo, and the product filtered to remove sediments, to yield 28.77 g (93%) of product as a pale yellow oil.

Xylenes may be replaced with other suitable solvents, for example ethylbenzene.

EXAMPLE 3

N,N-di-n-octyl-2-(di-n-octylamino)acetamide

To a rapidly stirred solution of 32.62 g of di-n-octylamine in 100 mL of acetonitrile, is added 7.62 g of 2-chloroacetyl chloride over a 1 hour period. The mixture is stirred at ambient temperature for 3 hours, followed by the addition of 15.91 g of sodium carbonate and 0.63 g of potassium iodide. The mixture is heated at reflux for 24 hours. After cooling, the mixture is partitioned between 250 mL of dichloromethane and 250 mL of water. The aqueous phase is further extracted with 250 mL of dichloromethane, and the combined organic extract is washed with water (100 mL), then brine (100 mL), dried over anhydrous sodium sulfate, and the solvent removed in vacuo. The resulting residue is partitioned between hexanes (300 mL) and acetonitrile (250 mL). After filtering to remove undissolved solids, the phases are separated and the yellow hexanes phase is washed with 2 portions (100 mL each) of acetonitrile. The hexanes are removed in vacuo to give the product as a waxy orange oil.

EXAMPLE 4

Diethylenetriamine penta-N,N-di-n-octylacetamide

A mixture of 31.8 g of 2-chloro-N,N-dioctylacetamide, 2.08 g of diethylenetriamine and 10.6 g of sodium carbonate in 150 mL of N,N-dimethylacetamide is heated at 150° C. for 48 hours. After cooling, it is washed with water, extracted with hexanes, then dried over sodium sulfate. The hexanes are removed in vacuo to give 30.6 g of the product as a dark brown liquid.

EXAMPLE 5

Ethylenediamine tetra-N-oleylacetamide

To a rapidly stirred mixture of oleylamine (118.5 g), diether (200 mL), $Na_2CO_3$ (50.29 g) and water (500 mL) is added chloroacetyl chloride (54.16 g) dropwise over 60 min. Intermittent cooling is applied to maintain temperature between 10-15° C. After completion of addition, the mixture is stirred for 60 min, and the phases are allowed to separate. Analysis (H-NMR) of a sample of the upper ether layer indicates that a small amount of amine is not reacted. Additional $Na_2CO_3$ (7 g) and water (50 mL) is added, followed by chloroacetyl chloride (7 g). The upper ether phase is removed, the aqueous phase extracted with additional ether (200 mL), and the combined organic phase is washed with water (2×125 mL portions), saturated NaCl (125 mL), dried over anh. $Na_2SO_4$, and the solvent removed in vacuo to give 149 g of 2-chloro-N-oleylacetamide.

A mixture of ethylenediamine (1.01 g), 2-chloro-N-oleylacetamide (23.13 g), N,N-dimethylacetamide (50 mL) and $Na_2CO_3$ (25.8 g) is heated for 20 hours at 120-130° C. After cooling, the reaction mixture is partitioned between diethyl ether (250 mL) and water (250 mL). The ether layer is washed with water (3×100 mL), saturated NaCl (100 mL), dried over anh. $Na_2SO_4$, and the solvent removed in vacuo to give 20.4 g of the tetra-alkylated product.

EXAMPLE 6

The following compounds are prepared according to the methods described herein.

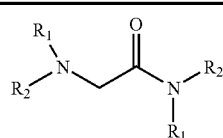

| $R_1$ | $R_2$ | physical form |
|---|---|---|
| n-octyl | n-octyl | liquid (Ex. 3) |

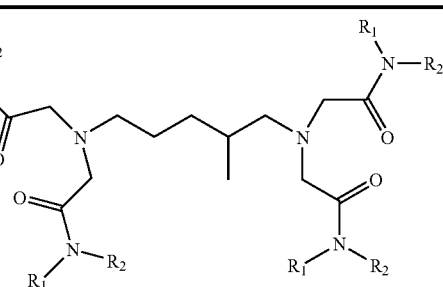

| $R_1$ | $R_2$ | physical form |
|---|---|---|
| 2-ethylhexyl | 2-ethylhexyl | liquid |
| n-octyl | n-octyl | liquid (Ex. 2) |
| oleyl | hydrogen | wax (Ex. 5) |
| n-octyl | hydrogen | wax (Ex. 1) |
| t-octyl | hydrogen | solid |
| dodecyl | hydrogen | solid |
| $C_{12}$-$C_{15}$ | hydrogen | syrup |
| $C_{18}$-$C_{24}$ | hydrogen | syrup |

| $R_1$ | $R_2$ | physical form |
|---|---|---|
| n-octyl | n-octyl | liquid |
| t-octyl | hydrogen | resin |
| 2-ethylhexyl | 2-ethylhexyl | liquid |

| $R_1$ | $R_2$ | physical form |
|---|---|---|
| t-octyl | hydrogen | resin |

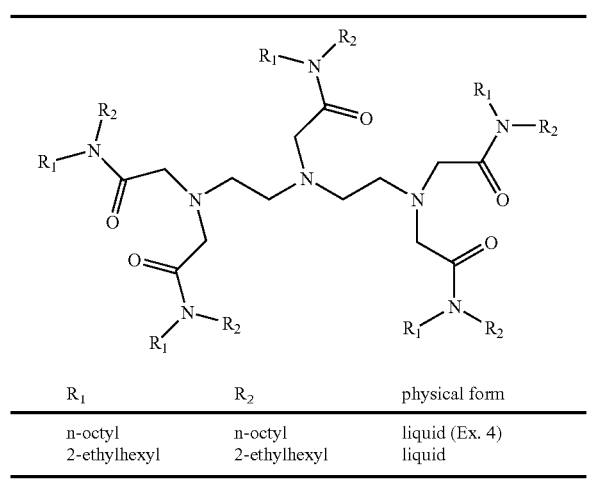

| $R_1$ | $R_2$ | physical form |
|---|---|---|
| n-octyl | n-octyl | liquid (Ex. 4) |
| 2-ethylhexyl | 2-ethylhexyl | liquid |

EXAMPLE 7

Antiwear properties are measured on a PCS Instruments Mini-Traction Machine, modified with a Pin-on-Disc attachment, in which a stationary pin (500×500 microns) is held against a rotating disc, with a fixed load applied at a constant temperature. Wear is measured as the displacement of the pin, due to loss of material from the pin. The test oil is a zero S, very low P automotive engine oil, fully formulated except that no antiwear additive is included. The reaction test conditions are 10N load, oil temperature 100° C. Wear data is recorded for 60 min, and the average wear rate is reported here as the linear regression slope of the wear curve.

| Oil | Wear Rate |
|---|---|
| test oil (no antiwear additive) | 279 microns/hr |
| test oil + 1.2% ZDDP | 3.0 microns/hr |
| test oil + 1% additive of Example 2 | 16 microns/hr |

ZDDP is zinc dialkyl dithiophosphate—a secondary ZDDP at 1.2% provides 0.1% P.

What is claimed is:

1. A lubricant composition having improved antiwear or friction properties comprising
a lubricating oil for internal combustion engines and
an effective antiwear or friction modifying amount of one or more additive compounds selected from the group consisting of
N-alkylaminoacetamide compounds of formula (I) or (II) and
alkylenedi-, alkylenetri- or alkylenetetra-amine acetamide compounds of formula (III)

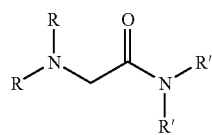

(I)

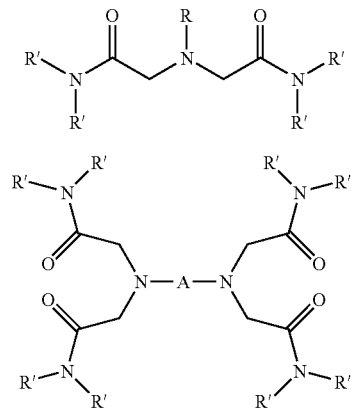

(II)

(III)

where
A is alkylene of from 2 to 6 carbon atoms or is a group

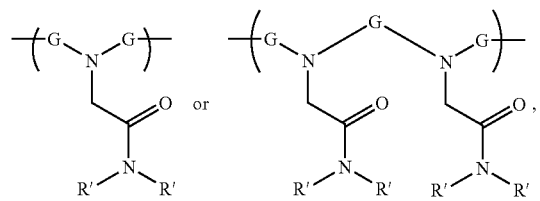

G, each independently, is alkylene of 2 to 6 carbon atoms,
R, each independently, is alkyl or alkenyl of 1 to 8 carbon atoms and
R', each independently, is hydrogen or alkyl or alkenyl or 1 to 24 carbon atoms, where if an amide nitrogen is mono-substituted by alkyl or alkenyl, said alkyl or alkenyl is from 8 to 24 carbon atoms, where if an amide nitrogen is disubstituted by alkyl or alkenyl, the total carbon atoms of said alkyls or alkenyls combined are from 8 to 18 carbon atoms, and where each amide nitrogen is either mono- or disubstituted by alkyl or alkenyl and
where the compounds of formula (I), (II) or (III) are present from about 0.15% to about 10% by weight, based on the weight of the lubricant.

2. A composition according to claim 1 comprising one or more compounds selected from the group consisting of N-alkylaminoacetamide compounds of formula (I).

3. A composition according to claim 1 comprising one or more compounds selected from the group consisting of N-alkylaminoacetamide compounds of formula (I) where if the amide nitrogen is disubstituted by alkyl or alkenyl, the total carbon atoms of said alkyls or alkenyls combined are from 14 to 18 carbon atoms.

4. A composition according to claim 1 comprising one or more compounds selected from the group consisting of N-alkylaminoacetamide compounds of formula (II).

5. A composition according to claim 1 comprising one or more compounds selected from the group consisting of N-alkylaminoacetamide compounds of formula (II) where if the amide nitrogen is disubstituted by alkyl or alkenyl, the total carbon atoms of said alkyls or alkenyls combined are from 14 to 18 carbon atoms.

6. A composition according to claim 1 comprising one or more compounds selected from the group consisting of alkylenedi-, alkylenetri- or alkylenetetra-amine acetamide compounds of formula (III).

7. A composition according to claim 1 comprising one or more compounds selected from the group consisting of alkylenedi-, alkylenetri- or alkylenetetra-amine acetamide compounds of formula (III) where A and G are selected from the group consisting of ethylene, propylene, hexamethylene and 2-methylpentylene.

8. A composition according to claim 1 where each R' is independently a straight or branched chain alkyl or alkenyl of 7 to 9 carbon atoms.

9. A composition according to claim 1 where one R' of each amide is hydrogen and the other is straight or branched chain alkyl or alkenyl of 14 to 18 carbon atoms.

10. A composition according to claim 1 where each R' is the same and is a straight or branched chain alkyl or alkenyl of 7 ot 9 carbon atoms.

11. A composition according to claim 1 where the compounds of formula (I), (II) and (III) are selected from the group consisting of

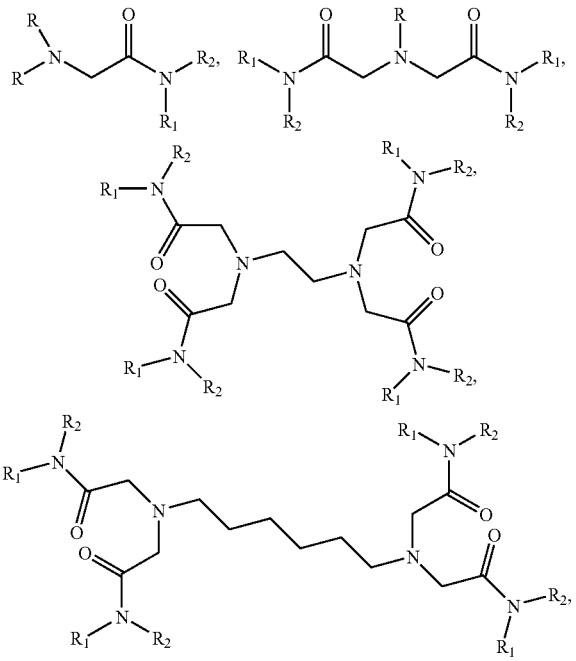

-continued

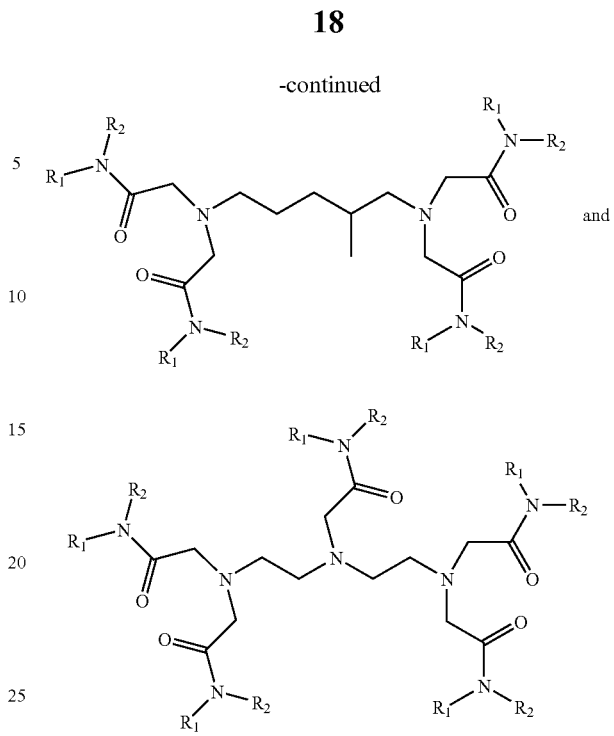

where R is n-octyl and each of $R_1$ and $R_2$ are 2-ethythexyl or n-octyl or one of $R_1$ and $R_2$ is hydrogen and the other is oleyl, n-octyl, t-octyl or dodecyl.

12. A composition according to claim 1 where the compounds of formula (I), (II) or (III) are soluble to a level of 2% by weight, based on the weight of the lubricant at room temperature.

13. A composition according to claim 1 where the compounds of formula (I), (II) or (III) are soluble to a level of 1% by weight, based on the weight of the lubricant at room temperature.

14. A composition according to claim 1 where the compounds of formula (I), (II) or (III) are present from about 0.15% to about 7% by weight, based on the weight of the lubricant.

* * * * *